US00PP21553P2

(12) United States Plant Patent
Lyrene

(10) Patent No.: US PP21,553 P2
(45) Date of Patent: Dec. 7, 2010

(54) SOUTHERN HIGHBUSH BLUEBERRY PLANT NAMED 'FL01-173'

(50) Latin Name: ***Vaccinium corymbosum* L.**
Varietal Denomination: FL01-173

(75) Inventor: Paul M. Lyrene, Micanopy, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/587,285

(22) Filed: Oct. 5, 2009

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu
(74) *Attorney, Agent, or Firm*—Jondle & Associates, P.C.

(57) ABSTRACT

A southern highbush blueberry (*Vaccinium corymbosum* L.) variety particularly distinguished by a low chilling requirement, very upright growth habit, vigorous early-spring leafing, early ripening (50% ripe berries in north Florida around April 24), very open berry cluster; and berries that are large and firm, somewhat darker in color, have good flavor, texture, and keeping quality, and have a small, dry picking scar.

2 Drawing Sheets

STATEMENT REGARDING FEDERALLY SPONSORED RESEARCH

Figure 1:
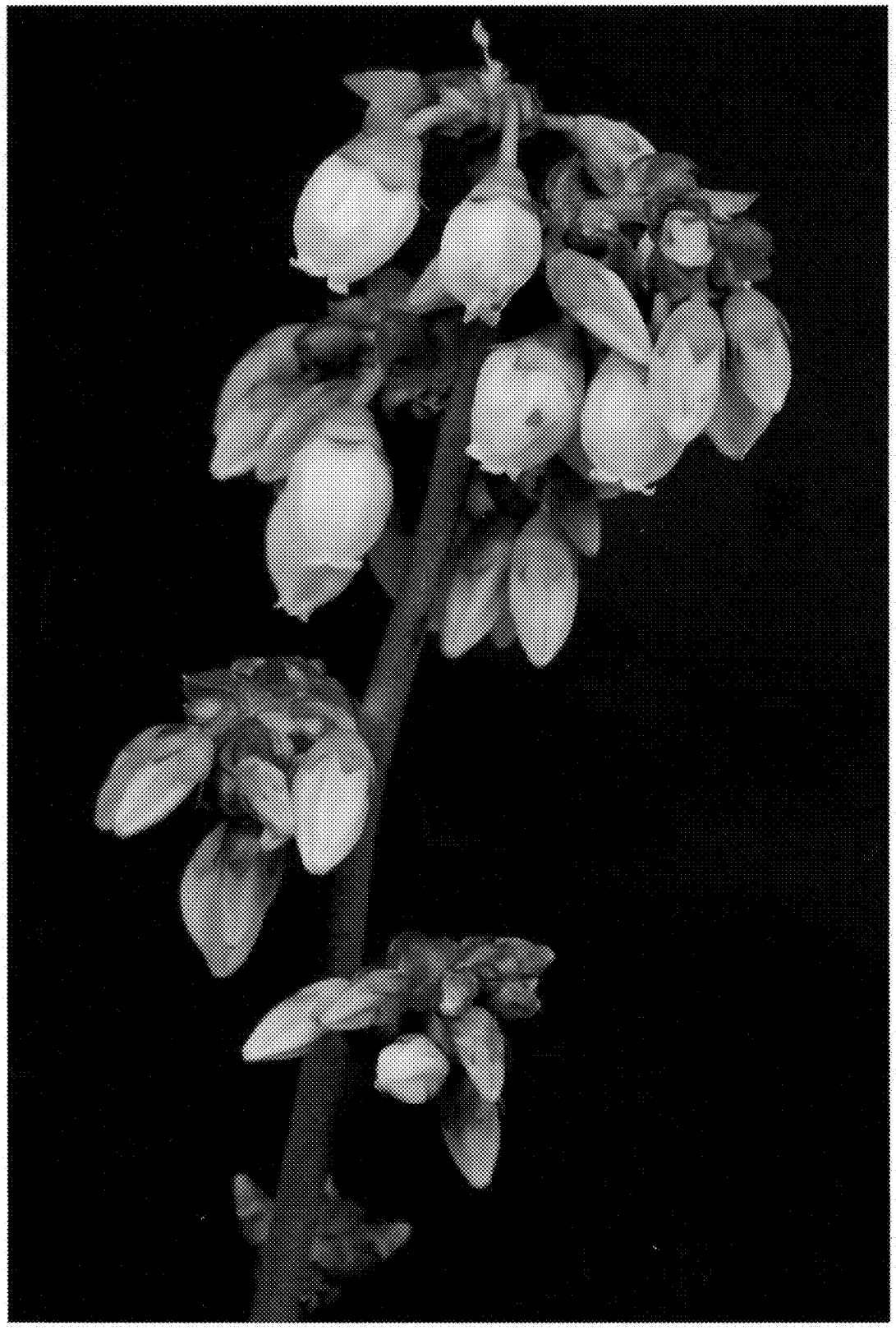

The present invention was supported in part by funds from the U.S. Government. The U.S. Government therefore may have certain rights in the invention.

Genus and species: *Vaccinium corymbosum* L.

Variety denomination: 'FL01-173'.

BACKGROUND OF THE NEW PLANT

The invention relates to a new and distinct variety of southern highbush blueberry (*Vaccinium corymbosum* L.) hybrid plant named 'FL01-173.''FL01-173' is a southern highbush blueberry clone distinguished by its low chilling requirement, its vigorous, upright growth habit, and by its firm, sweet berries that ripen from mid-April through early May when grown in north Florida. Several thousand plants of 'FL01-173' have been propagated by softwood cuttings at Gainesville, Fla., and the resulting plants have all been phenotypically indistinguishable from the original plant. Contrast is made to 'Star' (U.S. Plant Pat. No. 10,675), an important variety widely planted in Florida and Georgia for early-season blueberry production. The new variety is important because it is more vigorous and upright in growth habit than 'Star' and has a higher yield potential. It has a more open fruit cluster than 'Star' and the berries can be mechanically harvested with less damage than 'Star' berries.

'FL01-173' originated as a seedling from the cross 'FL98-183' (unpatented)×'FL98-133' (unpatented) made as part of the University of Florida breeding program in a greenhouse at Gainesville, Fla. in February 1998. The seedling was first fruited in a high-density field nursery in the spring of 2000. After the second year of fruiting in the field, in the spring of 2001, 'FL01-173' was propagated by softwood cuttings in June 2001, and an experimental 20-plant test plot was established as part of a variety test at Windsor, Fla. in March 2002. Based on the growth and yield of this plot, 'FL01-173' was repropagated by softwood cuttings in June 2004, and an experimental test plot of about 500 plants was planted the following winter on a blueberry farm at Waldo, Fla. This plot was observed from flowering through fruit ripening each year, and no mutations or off-type plants have been observed.

SUMMARY OF THE INVENTION

The following are the most outstanding and distinguishing characteristics of this new cultivar when grown under normal horticultural practices in Florida.

1. A low chilling requirement;
2. Very upright growth habit;
3. Vigorous early-spring leafing;
4. Early ripening (50% ripe berries in north Florida around April 24);
5. Very open berry cluster; and
6. Berries that are large and firm, are somewhat darker in color, have good flavor, texture, and keeping quality, and have a small, dry picking scar.

DESCRIPTION OF THE PHOTOGRAPHS

The color chart used in this specification is "The Pantone Book of Color" (by Leatrice Eiseman and Lawrence Herbert, Harry N. Abrams, Inc., Publishers, New York, 1990). Where colors in the drawings differ from the Pantone color designations in the descriptions, the Pantone color designations are accurate. The colors shown are as true as can be reasonably obtained by conventional photographic procedures.

FIG. 1 shows several clusters of opening flowers during the early stages of flowering in February. The unopened flowers are pink in color here but are more nearly white if the weather is warmer during flowering, and the pink fades to white by the time of anthesis.

Figure 2:
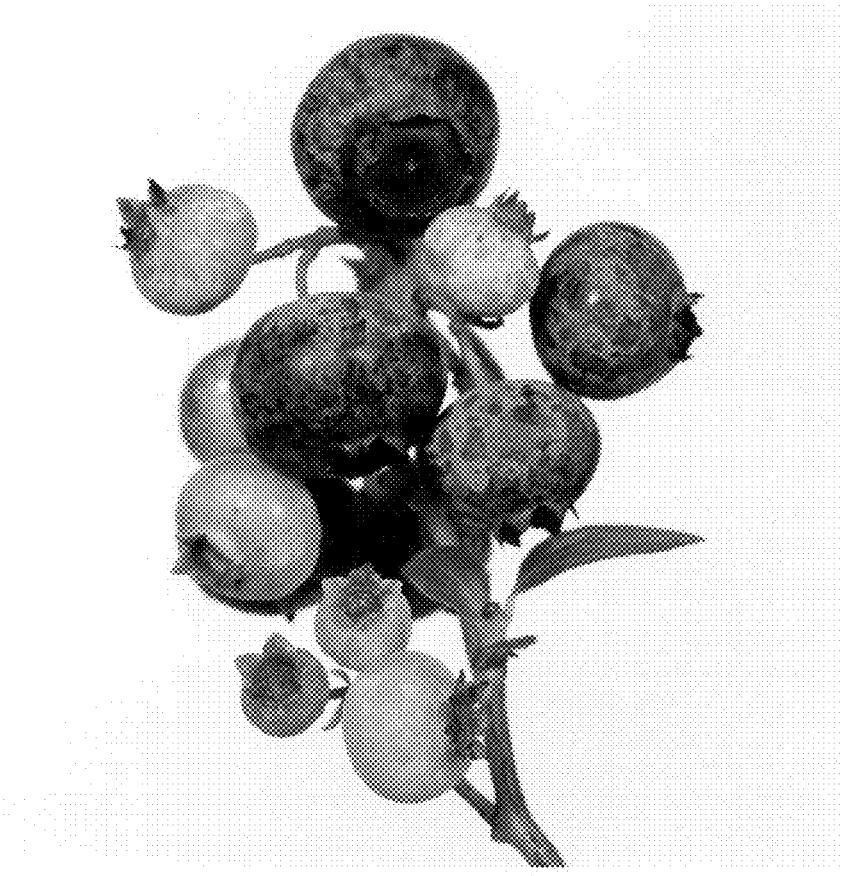

FIG. 2 shows several clusters of berries at various stages of ripening. The freckling pattern is due to naturally occurring minerals in the water being used in overhead irrigation of the plants and is not an inherent feature of the berries. The long pedicels, which produce an open berry cluster, can be seen.

The berries of 'FL01-173' are much more synchronous in ripening than is implied by this figure.

Figure 3:
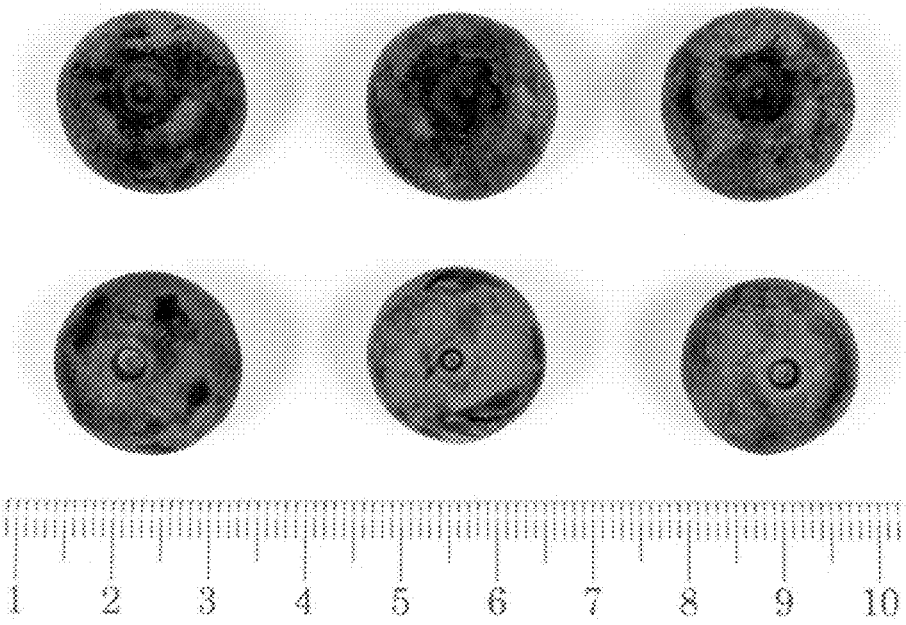

FIG. 3 shows berries at close range. The small, dry picking scars and the rather dark color of the berries is shown.

DESCRIPTION OF THE NEW CULTIVAR

The following detailed description sets forth the distinctive characteristics of 'FL01-173.' The data which define these characteristics were collected from asexual reproductions carried out in Florida. The plant history was taken on 3½-year-old plants. The following descriptions relate to plants grown in the field in north Florida (Windsor, Fla.). Color designations are from "The Pantone Book of Color" (by Leatrice Eiseman and Lawrence Herbert, Harry N. Abrams, Inc., Publishers, New York, 1990). Where the Pantone color designations differ from the colors in the drawings, the Pantone colors are accurate.

DETAILED BOTANICAL DESCRIPTION

Classification:

*Family.*—Ericaceae.

*Botanical.*—*Vaccinium corymbosum* L.

*Common name.*—Southern Highbush Blueberry.

Parentage:

*Female parent.*—'FL84-33,' a proprietary southern highbush blueberry plant (unpatented).

*Male parent.*—'FL98-183,' a proprietary southern highbush blueberry plant (unpatented).

*Market class.*—'FL01-173' produces southern highbush blueberries suitable for both the fresh and processed fruit markets.

Plant:

*General.*—Bush characteristics were taken from a plot of one-hundred 3½-year-old plants growing in a test plot in a commercial field near Waldo in northeast Florida.

*Plant height.*—2.3 m.

*Canopy* (*diameter measured at widest part of the bush*).—1.6 m.

*Plant vigor.*—High; more vigorous than 'Star'.

*Growth habit.*—Strongly upright.

*Flower bud density* (*number*) *along flowering twigs in January.*—Very high.

*Twigginess.*—Medium.

*Tendency toward evergreenness.*—Medium.

*Productivity.*—In northeast Florida, 'FL01-173' produces 5 to 8 pounds of berries per bush on plants 3 years old or older.

*Chilling requirement.*—200 hours below 7° C.

*Cold hardiness.*—Flowers and fruit are hardy to −3° C.; the plant is hardy to −15° C. during winter dormancy

*Ease of propagation.*—'FL01-173' is easy to propagate from softwood cuttings; the plants survive and grow well in nursery beds.

Trunk and branches:

*Suckering tendency.*—Low to medium; 4-year-old plants have an average of five major canes rising from a crown 30 cm in diameter.

*Surface texture* (*of strong, 6-month-old shoots observed in June*).—Smooth.

*Surface texture* (*of 3-year-old and older wood*).—Rough due to exfoliation and production of vertical cracks.

*Color of new twigs observed in June in the field.*—"Tarrogon," Pantone 15-0326.

*Color of 3-year-old canes.*—"Sheepskin," Pantone 14-1122.

*Internode length on strong, upright shoots measured in June.*—2.8 cm.

Leaves:

*Length, mean* (*including petiole, from tip of petiole to end of blade*).—5.7 cm.

*Width, mean* (*at widest point*).—2.8 cm.

*Shape.*—Ovate, terminating in a very short dew tip, 0.02 cm long, which is visible with a 15× microscope.

*Margin.*—Entire, except for the presence of sessile glands along lower part of leaf blade, about 5 on each side of the petiole.

*Color.*—Upper surface: "Chive," Pantone 19-0323. Lower surface: "Forest Green," Pantone 17-0230.

*Pubescence on upper surface of leaves.*—Numerous short, white hairs along the midrib.

*Pubescence on the lower surface of leaves.*—Absent.

*Pubescence on margins.*—Absent.

*Relative time of leafing versus flowering.*—In commercial fields in north Florida, where it is sprayed with hydrogen cyanamide in midwinter, 'FL01-173' begins to produce new leaves at the time of full bloom.

Flowers:

*Arrangement.*—Flowers are arranged alternately along a short, leafless, deciduous branch.

*Fragrance.*—Little or none.

*Shape.*—Urceolate.

*Flowering period.*—Mean date of 50% open flowers in Windsor, Fla. is February 3.

*Cluster* (*tight, medium, loose*).—Loose.

*Average number of flowers per cluster.*—Median of 5.

*Pedicel.*—Length at time of anthesis: 0.5 cm. Color: "Aurora Pink," Pantone 15-2217 on side most exposed to light.

*Peduncle.*—Length at time of anthesis: Highly variable; median is 0.7 cm. Color: "Aurora Pink," Pantone 15-2217 on side most exposed to light.

*Calyx.*—Surface texture: Smooth. Color at anthesis: "Parrot Green," Pantone 15-0341.

*Corolla.*—Diameter of tube (at widest point): 0.6 cm. Aperture diameter: 0.2 cm. Surface texture: Smooth. Color at anthesis: White. Length (from pedicel attachment point to corolla tip excluding the pedicel): Median 0.9 cm.

Reproductive Organs:

*Style length* (*top of ovary to stigma tip*).—0.9 cm.

*Location of tip of stigma relative to lip of the corolla.*—Stigma tip is even with the tip of the corolla lip.

*Pollen.*—Abundance of shed: Very high. Staining with 2% acetocarmine (a measure of potential pollen fertility): 99%. Color of dried pollen: "Winter White," Pantone 11-0507.

*Self fruitfulness.*—Low to medium; planting in field configurations that promote cross pollination with other southern highbush clones is recommended for all southern highbush blueberry plants in Florida.

Fruit:

*Mean date of first commercial harvest* (*25% of berries ripe*).—April 10.

*Mean date of mid-harvest.*—April 24.

*Mean date of last harvest.*—May 5.

*Diameter of calyx aperture on mature berry.*—0.7 cm.

*Size and shape of calyx lobes on mature berry.*—Irregular but large; the calyx lobes tend to jut outward from the berry surface.

*Pedicel length on ripe berry.*—Median is 0.3 cm.

*Peduncle length on ripe berry.*—Variable; median is 0.4 cm.

*Detachment force for ripe berries.*—Light to medium.

*Number of berries per cluster.*—Median is 6.

Berry:

*Cluster* (*tight, medium, or loose*).—Loose.

*Mean weight* (*on well-pruned plants*).—2.4 g per berry compared to 2.0 g per berry for 'Star.'

*Height.*—1.5 cm.

*Width.*—1.9 cm.

*Shape.*—Subglobose; wider than tall.

*Surface color of immature berries with bloom.*—"Frozen Dew," Pantone 13-0513.

*Surface color of immature berries, wax not disturbed.*—"Frozen Dew," Pantone 13-0513.

*Surface color of mature berries while on the plant.*—"Vapor Blue," Pantone 14-4203.

*Surface color of ripe berry after polishing.*—Shiny black.

*Surface wax.*—Low to medium in amount and persistence.

*Pedicel scar.*—Medium to small size and dry.

*Firmness.*—High.

*Flavor.*—Mild, with some sugar and some acid.

*Texture.*—Good; small seeds and thin skinned.

Seeds:

*Color of dried seeds.*—"Tobacco Brown," Pantone 17-1327.

*Weight of well-developed dried seed.*—0.4 mg per seed.

*Length of well-developed dried seed* (*mean*).—0.15 cm.

Resistance to diseases, insects, and mites: 'FL01-173' has grown vigorously and shows good bush survival in the field. It appears to have above-average resistance to root rot (*Phytophthora cinnamomi*) and stem blight (*Botryosphaeria dothidia*). The plants have shown no signs of cane canker (*Botryosphaeria corticis*) susceptibility in the field. The fungal leaf spots that are common on highbush blueberries grown in Florida are easily controlled by approved fungicides. In the absence of fungicide applications, 'FL01-173' leaves appear to have better leaf-spot resistance than most other Florida southern highbush blueberry cultivars.

COMPARISON WITH PARENTAL AND KNOWN CULTIVARS

'FL01-173' differs from the proprietary female (seed) parent 'FL84-33' (unpatented) in that 'FL01-173' ripens earlier, has a larger berry, and a more open berry cluster than 'FL84-33.' In addition, 'FL01-173' is more vigorous and more upright than 'FL84-33.'

'FL01-173' differs from the male (pollen) parent 'FL98-183' (unpatented) in that 'FL01-173' has a larger, earlier-ripening berry than 'FL98-183.'

'FL01-173' differs from the commercial variety 'Star' (U.S. Plant Pat. No. 10,675), an important variety widely planted in Florida and Georgia for early-season blueberry production, in that 'FL01-173' is more vigorous and upright in growth habit than 'Star' and has a higher yield potential. In addition, 'FL01-173' has a more open fruit cluster than 'Star' and the berries can be mechanically harvested with less damage than 'Star' berries.

I claim:

1. A new and distinct variety of southern highbush blueberry plant as shown and described herein.

* * * * *